(12) United States Patent
Hershkowitz et al.

(10) Patent No.: US 7,183,328 B2
(45) Date of Patent: Feb. 27, 2007

(54) METHANOL MANUFACTURE USING PRESSURE SWING REFORMING

(75) Inventors: Frank Hershkowitz, Liberty Corner, NJ (US); James R. Lattner, Seabrook, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 469 days.

(21) Appl. No.: 10/738,782

(22) Filed: Dec. 17, 2003

(65) Prior Publication Data

US 2005/0137269 A1 Jun. 23, 2005

(51) Int. Cl.
*C07C 27/00* (2006.01)
*C07C 1/00* (2006.01)

(52) U.S. Cl. .................. 518/709; 518/700; 518/702; 518/704; 518/705; 518/713; 518/714; 518/715; 585/640

(58) Field of Classification Search .......... 518/700, 518/702, 704, 705, 709, 713, 714, 715; 585/640
See application file for complete search history.

(56) References Cited

U.S. PATENT DOCUMENTS

| | | | |
|---|---|---|---|
| 1,726,877 A | 9/1929 | Battig | |
| 2,313,157 A | 3/1943 | Linder | |
| 2,556,835 A | 6/1951 | Barr | |
| 3,429,678 A | 2/1969 | Milbourne et al. | |
| 4,200,682 A | 4/1980 | Sederquist | |
| 4,240,805 A | 12/1980 | Sederquist | |
| 4,293,315 A | 10/1981 | Sederquist | |
| 4,499,327 A | 2/1985 | Kaiser | |
| 4,642,272 A | 2/1987 | Sederquist | |
| 4,816,353 A | 3/1989 | Wertheim et al. | |
| 6,302,188 B1 | 10/2001 | Ruhl et al. | |
| 6,495,610 B1* | 12/2002 | Brown | 518/706 |
| 6,890,962 B1 | 5/2005 | O'Rear et al. | |
| 7,045,553 B2 | 5/2006 | Hershkowitz | |
| 2003/0181322 A1 | 9/2003 | Chang et al. | |
| 2003/0235529 A1 | 12/2003 | Hershkowitz et al. | 423/652 |
| 2004/0170558 A1 | 9/2004 | Hershkowitz | 423/652 |

OTHER PUBLICATIONS

Stanford Research Institute (SRI) Consulting, *Process Economics Program Report* 148A, Synthesis Gas, pp. 1-75 (Nov. 1995).

* cited by examiner

*Primary Examiner*—J. Parsa (57) ABSTRACT

A process for producing methanol is described in which a hydrocarbon is steam reformed in a reforming zone, and during the reforming stage, of a cyclic steam reformer having a reforming stage and a regeneration stage, the steam reforming being conducted under conditions effective to produce a first effluent stream containing synthesis gas. A fuel and an oxygen-containing gas are combusted in the regeneration stage of the reformer so as to reheat the reforming zone to a temperature sufficient for the reforming stage and generate a flue gas. At least part of the first effluent stream is contacted with a methanol synthesis catalyst under conditions effective to convert synthesis gas to methanol and form a methanol-containing stream and a tail gas stream comprising unreacted carbon monoxide and hydrogen. Hydrogen is separated from at least one of the first effluent stream and the tail gas stream and at least part of the hydrogen is recycled as part of the fuel for the regeneration stage of the cyclic steam reformer.

40 Claims, 3 Drawing Sheets

METHANOL MANUFACTURE USING PRESSURE SWING REFORMING

FIELD

The present invention relates broadly to the manufacture of methanol. More particularly the invention relates to a process for making methanol that integrates pressure swing reforming to convert a hydrocarbon, such as methane, to synthesis gas with conversion of the synthesis gas to methanol.

BACKGROUND

Methanol is a major chemical raw material. Present global consumption is about 27 million tons per year. Major uses of methanol include the production of acetic acid, formaldehyde, and methy-t-butylether. The latter, an oxygenate additive to gasoline, accounts for about a third of all use. Worldwide demand for methanol is expected to increase as much as five fold over the next decade as potential new applications become commercialized. Such applications include the conversion of methanol to gasoline, the conversion of methanol to light olefins, the use of methanol for power generation, and the use of methanol for fuel-cell powered automobiles.

In general, methanol synthesis is based on the equilibrium reactions of synthesis gas (often abbreviated to "syngas"), namely reactions (1) and (2):

$$CO+2H_2 \leftrightarrows CH_3OH \quad (1)$$

$$CO_2+3H_2 \leftrightarrows CH_3OH+H_2O \quad (2)$$

Synthesis gas is defined as a gas comprising primarily carbon monoxide (CO), carbon dioxide ($CO_2$) and hydrogen ($H_2$). Other gases present in synthesis gas typically include methane ($CH_4$), and small amounts of light paraffins, such as ethane and propane. One way of characterizing the composition of a synthesis gas stream for the production of methanol is to account for the $CO_2$ present in the synthesis gas stream. The syngas number (SN) is defined as follows:

$$SN=(H_2-CO_2)/(CO+CO_2)$$

The forward reactions (1) and (2) are exothermic, that is, they result in the formation of net heat. Also, the forward reactions (1) and (2) generate less volumes of MeOH (gas) than the volumes of feed (gas) used to form the methanol. Therefore, to maximize methanol yields, i.e., force reactions (1) and (2) to the right, the process requires low temperatures and high pressures for high conversion. Still, a typical methanol reactor will convert only about 20% to 60% of the synthesis gas fed to the reactor in a single pass through. To obtain higher conversions the unreacted synthesis gas is separated from the product methanol and recycled back to the reactor or directed to a second reactor to produce additional methanol.

The initial step in the production of methanol is to produce synthesis gas from a hydrocarbon-containing feed, typically a methane-containing feed, such as natural gas or refinery off-gas. The associated costs of producing the synthesis gas currently account for over half of the capital investment in the methanol plant. Known methods for producing synthesis gas include steam reforming, non-catalytic and catalytic partial oxidation and autothermal reforming.

In a steam reforming process, steam is reacted with a hydrocarbon containing feed over a catalyst, such as nickel, nickel oxide, cobalt oxide, chromia and/or molybdenum oxide, to produce a hydrogen-rich synthesis gas. The general stoichiometry, as illustrated for methane, is:

$$CH_4+H_2O \leftrightarrows CO+3H_2 \quad (3)$$

Typically, an excess of steam is used to drive the equilibrium to the right.

Because of the high endothermicity of the reaction, steam reforming is typically carried out in large furnaces, in which the catalyst is packed into tubes. The tubes must withstand the high pressure of the produced synthesis gas, while transmitting heat at temperatures approaching 1000° C. As described in Stanford Research Institute International Report No 148A (1995), steam reforming process efficiency, defined as the heat of combustion of product synthesis gas divided by the heat of combustion of reforming feed and furnace fuel, is approximately 79%, while the space velocity, defined as Standard Cubic Feet per Hour of $C_1$-equivalent feed/$ft^3$ of catalyst bed is 690 $hr^{-1}$. Unfortunately, steam reforming furnaces occupy a very large volume of space, orders of magnitude greater than the tube volume, such that low productivity limits the economic attractiveness of the process.

The partial oxidation process involves the partial oxidation of a hydrocarbon containing feed in the gas phase. The process can be carried out with or without a catalyst. In non-catalytic partial oxidation the feed components are introduced to a burner where they combust with sub-stoichiometric oxygen to produce a synthesis gas mixture. Catalytic partial oxidation comprises passing a gaseous hydrocarbon mixture, and oxygen, preferably in the form of air, over a reduced or unreduced composite catalyst, conveniently containing one or more transition metals. The ideal partial oxidation reaction, as illustrated for methane, is:

$$CH_4+\tfrac{1}{2}O_2 \leftrightarrows CO+2H_2 \quad (4)$$

However, gas-phase reaction kinetics tend to over-oxidize some of the feed, resulting in excessive heat generation and substantial yield of $H_2O$, $CO_2$, and unreacted hydrocarbons that may leave the reactor as soot. For these reasons, when gas phase partial oxidation chemistry is applied to clean feeds, it is preferred to add steam to the feed and add a bed of steam reforming catalyst to the bottom of the gas phase partial oxidation reactor vessel. This combination of gas phase partial oxidation and steam reforming is called autothermal reforming. The heat needed for steam reforming is provided in-situ from the excess heat generated by the gas phase partial oxidation reactions.

Autothermal reforming can be substantially more compact than steam reforming because furnaces are not used to provide heat of reaction. Embodiments of autothermal reforming presently under development for gasoline-powered fuel cell vehicles make use of a catalytic partial oxidation step, which can impart even greater compactness to the autothermal reforming process. The thermal efficiency of autothermal reforming reactors are generally in the range of 90%. While autothermal reforming based on catalytic partial oxidation may have high productivity (gas hourly space velocity on order of $10^4$ as $C_1$-equivalent), conventional partial oxidation-based autothermal reforming has a space velocity very similar to that of steam reforming (about $10^3$ $hr^{-1}$). However, autothermal reforming requires a source of oxygen. In the fuel cell vehicle case, this oxygen in typically provided as low-pressure air, which results in a nitrogen-diluted, low-pressure synthesis gas. In refinery or chemicals embodiments, this oxygen is typically provided as purified $O_2$, but the cost of air separation can be greater than the cost of the autothermal reforming process.

U.S. Pat. Nos. 4,200,682, 4,240,805, 4,293,315, 4,642,272 and 4,816,353 to Sederquist teach a steam reforming process in which the heat of reforming is provided within the catalyst bed by cycling between combustion and reforming stages of a cycle. As described by Sederquist, the high quality of heat recovery within the reforming bed results in a theoretical efficiency of about 97%. However, the examples and commercial projections within these patents describe a process that operates at very low productivity, with space velocities of around 95 $hr^{-1}$ (as $C_1$-equivalent). Moreover, this process requires a compressor to compress the product synthesis gas to useful pressures.

Copending U.S. patent application Ser. No. 10/458,399 filed Jun. 10, 2003 describes an improved cyclic steam reforming process for producing synthesis gas. In this process, the reforming stage involves preheating a first zone to a temperature in the range of about 700° C. to 2000° C. and then introducing a 20° C. to 600° C. hydrocarbon-containing feed, along with steam and optionally $CO_2$ to the inlet of the first zone. The hydrocarbon is reformed into synthesis gas over a catalyst in the first zone and the synthesis gas is then passed to a second zone, where the synthesis gas is cooled to a temperature close to the inlet temperature of the hydrocarbon feed and is recovered. In the regeneration stage, an oxygen-containing gas and fuel are combusted near the interface of the two zones, producing a hot flue gas that travels across the first zone, thus re-heating that zone to a temperature high enough to reform the feed. Once heat regeneration is completed, the cycle is completed and reforming begins again. An advantage of this process is the ability to operate the reforming stage at a higher pressure than the regeneration stage, thus creating a pressure swing, and producing high pressure synthesis gas.

The present invention provides a process scheme for integrating a cyclic reforming process for producing synthesis gas, such as that disclosed U.S. patent application Ser. No. 10/458,399, with a process for converting the synthesis gas to methanol. The process scheme seeks to effect this integration in a manner that maximizes thermal efficiency and minimizes capital cost.

SUMMARY

In one aspect, the present invention resides in a process for producing methanol comprising:
(a) steam reforming a hydrocarbon in a reforming zone, and during the reforming stage, of a cyclic steam reformer having a reforming stage and a regeneration stage, said steam reforming being conducted under conditions effective to produce a first effluent stream containing synthesis gas;
(b) combusting a fuel and oxygen in the regeneration stage of the reformer so as to reheat said reforming zone to a temperature sufficient for the reforming stage and produce a flue gas;
(c) contacting at least part of said first effluent stream with a methanol synthesis catalyst under conditions effective to convert synthesis gas to methanol and form a methanol-containing stream and a tail gas stream comprising unreacted carbon monoxide and hydrogen; and
(d) separating hydrogen from at least one of said first effluent stream and said tail gas stream and recycling at least part of said hydrogen as part of said fuel for the regeneration stage of said cyclic steam reformer.

In one embodiment of the above process, the reforming stage is conducted at a higher pressure than the regeneration stage, thereby creating a pressure swing and facilitating the production of high pressure synthesis gas. Conveniently, the reforming stage is conducted at a pressure of about 1000 kPa to about 10,000 kPa, such as about 2000 kPa to about 7,500 kPa, whereas the regeneration stage is conducted at a pressure of about 100 kPa to about 2,000 kPa, such as about 200 kPa to about 1500 kPa.

Conveniently, the oxygen employed in said regeneration stage is provided as compressed air extracted from a gas turbine.

In a further aspect, the invention resides in a process for producing methanol comprising:
(a) providing a reforming reactor having a first zone comprising a reforming catalyst and a second zone comprising a packing material, said first and second zones being in fluid communication and said reformer being cyclable between a reforming stage and a regeneration stage;
(b) introducing a hydrocarbon and steam into the first zone of the reforming reactor during each reforming stage and steam reforming the hydrocarbon in said first zone under conditions effective to produce a first effluent stream containing synthesis gas;
(c) passing at least a portion of said first effluent stream from said first zone to said second zone and transferring heat from said first effluent stream to said packing material;
(d) withdrawing the first effluent stream from the second zone;
(e) introducing oxygen and fuel into the second zone of the reforming reactor during each regeneration stage under conditions to combust the fuel and reheat said first zone to a temperature sufficient for the reforming stage and produce a flue gas;
(f) contacting at least part of said first effluent stream with a methanol synthesis catalyst in a methanol synthesis reactor under conditions effective to convert synthesis gas to methanol and form a methanol-containing stream and a tail gas stream comprising unreacted carbon monoxide and hydrogen;
(g) separating hydrogen from at least one of said first effluent stream and said tail gas stream; and
(h) recycling at least part of the hydrogen separated in (g) as part of said fuel for the regeneration stage of said reforming reactor.

In yet a further aspect, the invention resides in an integrated process for producing olefins from a hydrocarbon in which at least part of the methanol produced according the processes described above is contacted with a molecular sieve catalyst under conditions effective to convert said methanol to an olefin-containing product.

DETAILED DESCRIPTION OF THE EMBODIMENTS

In the present invention cyclic steam reforming to produce synthesis gas is integrated with conversion of the synthesis gas to methanol and, in a preferred embodiment, with conversion of the methanol to light olefins, particularly ethylene and propylene.

In the process of the invention, a hydrocarbon, such as methane, is initially fed to a cyclic steam reformer having a reforming stage and a regeneration stage. During each regeneration stage, a fuel and oxygen are combusted so as to heat the reformer to a temperature sufficient for next reforming stage. During each reforming stage, the hydrocarbon is reacted with steam in the presence of a catalyst to produce an effluent stream containing synthesis gas. The effluent stream is then removed from the reformer and at least part of this stream is contacted with a methanol synthesis catalyst under conditions effective to convert synthesis gas to methanol and form a methanol-containing stream and a tail gas stream comprising unreacted carbon monoxide and hydrogen. By removing hydrogen from the effluent stream and/or the tail gas stream and recycling at least part of the hydrogen to provide fuel for the regeneration stage of the cyclic reformer, a cost and thermal efficient integration of the reforming and methanol synthesis processes can be achieved.

In one embodiment a pressure swing reforming process, such as that disclosed in U.S. Provisional Application No. 60/391,360, is employed so as to produce the synthesis gas at high pressure, such as about 1000 kPa to about 10,000 kPa, such as about 2000 kPa to about 7,500 kPa. In this way, the need to compress the synthesis gas prior to feeding to the methanol synthesis reactor can be reduced or eliminated.

Cyclic Steam Reforming

Figure 1A:
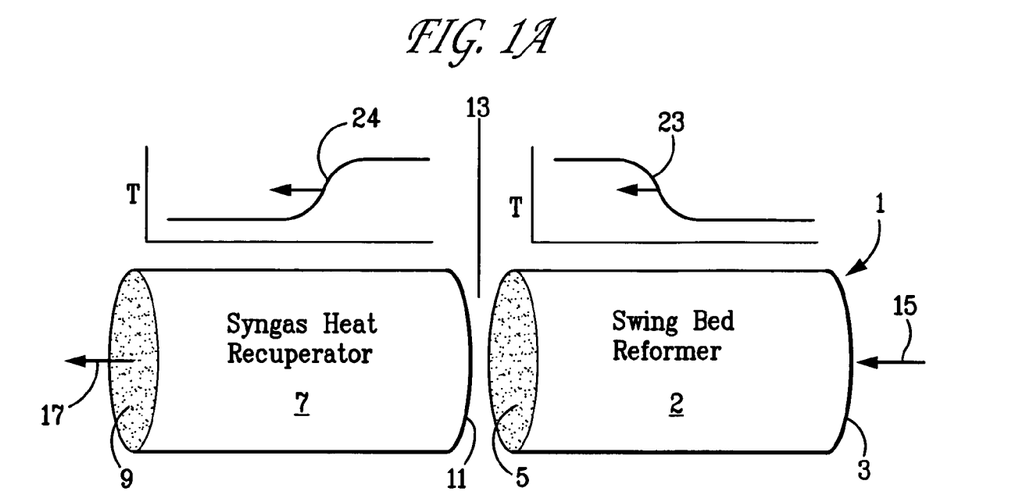
FIGS. 1a and 1b are schematic illustrations showing the basic reforming and regeneration stages of a pressure swing reforming process.
Figure 1B:
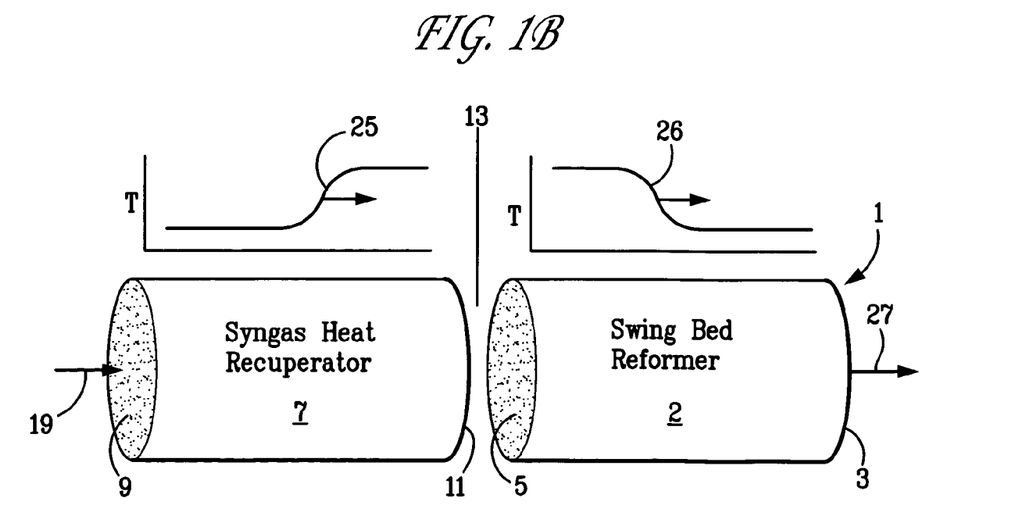

The two basic stages, the reforming stage and the regeneration stage, of a cyclic steam reforming process are illustrated diagrammatically in FIGS. 1(a) and 1(b) respectively.

Referring now to FIGS. 1(a) and 1(b), a cyclic steam reformer 1 comprises a first or reforming zone 2, called a swing bed reformer, and a second or recuperating zone 7, called a synthesis gas heat recuperator. The zones 2, 7 are in fluid communication and both include packing material, while the reforming zone 2 also includes catalyst for steam reforming. Though illustrated as separate reforming and regenerating zones, it is to be recognized that the pressure swing reforming apparatus may comprise a single reactor.

As shown in FIG. 1a, at the beginning of the reforming stage, the reforming zone 2 is at an elevated temperature, such as from about 600° C. to about 1200° C., and the recuperating zone 7 is at a lower temperature than the reforming zone 2, such as from about 300° C. to about 500° C. A hydrocarbon-containing feed is introduced via a conduit 15 into a first end 3 of the reforming zone 2 along with steam. Typically the temperature of the reforming fuel ranges from about 20° C. to about 600° C., such as from about 150° C. to about 450° C.

The hydrocarbon may be any material that undergoes the endothermic steam reforming reaction including methane, petroleum gases, petroleum distillates, kerosene, jet fuel, fuel oil, heating oil, diesel fuel and gas oil and gasoline. Preferably the hydrocarbon will be a gaseous material or one which will rapidly become substantially gaseous upon introduction into the reforming zone 2. Preferably, the steam will be present in proportion to the hydrocarbon in an amount that results in a steam to carbon ratio between about 1 and about 3 (considering only carbon in the hydrocarbon, not carbon in CO or $CO_2$ species that may be present).

During the reforming stage, the hydrocarbon feed stream picks up heat in the reforming zone 2 and is converted over the reforming catalyst to produce synthesis gas. As this stage proceeds, a temperature profile 23 is created based on the heat transfer properties of the system. Assuming the bed is designed with adequate heat transfer capability, this profile has a relatively sharp temperature gradient, which gradient will move across the reforming zone 2 as the stage proceeds.

Synthesis gas exits the reforming bed 2 through a second end 5 thereof at an elevated temperature and passes through the recuperating zone 7, entering through a first end 11 and exiting at a second end 9. The recuperating zone 7 is initially at a lower temperature than the reforming zone 2. As the synthesis gas passes through the recuperating zone 7, the synthesis gas is cooled to a temperature approaching the temperature of the recuperating zone substantially at the second end 9, which is approximately the same temperature as the regeneration feed introduced during the second, regeneration stage of the cycle via conduit 19 (e.g. from about 20° C. to about 600° C.). As the synthesis gas is cooled in the recuperating zone 7, a temperature gradient 24 is created and moves across the recuperating zone 7.

At the end of the reforming stage, the temperature gradients have moved substantially across the reforming zone 2 and the recuperating zone 7. The zones are sized so that the gradients move across both in comparable time during the reforming stage. The recuperating zone 7 is now at the high temperature, such as from about 1100° C. at the end 11 to about 500° C. at the end 9 and the reforming zone 2 is at lower temperature, except for the temperature gradients that exist near the exits of the respective zones. The temperature of the reforming zone 2 near the inlet end 3 has now been cooled to a temperature that approaches the temperature of the hydrocarbon feed that had been entering via conduit 15 (e.g. from about 20° C. to about 600° C.).

Towards the end of the reforming stage, the temperature at end 5 of the reforming zone is reduced and consequently the reforming performance deteriorates below acceptable conversion efficiencies. Reforming performance, as used herein, refers to the conversion of feed hydrocarbons into synthesis gas components of $H_2$, CO and $CO_2$. The term percent conversion, as used herein, is calculated as the percent conversion of the carbon in feed hydrocarbonaceous species into synthesis gas species of CO and $CO_2$. The term unconverted product hydrocarbons, as used herein, refers to product hydrocarbonaceous species that are not synthesis gas components of $H_2$, CO and $CO_2$. These typically include product methane, as well as feed hydrocarbons and the cracking products of feed hydrocarbons. The reforming stage is therefore normally terminated before the reforming performance deteriorates below acceptable limits. In practice, optimization of the overall reforming and synthesis gas utilization process will dictate a desired, time-averaged level of reforming conversion. That time-averaged level of reforming conversion is typically greater than 80%, preferably greater than 90%.

The point in time at which the reforming stage is ended, and thus the duration of the reforming stage, may be chosen (a) as a response to the time-varying performance of the reformer during each reforming stage; or (b) based on overall (time-averaged) performance or the system; or (c) fixed as a constant reforming stage duration. In embodiment (a), at least one feature of the operation is monitored that is correlated to the reforming performance. This feature may be a composition such as $CH_4$, $H_2$, or CO, or alternatively a temperature, such as the temperature at the end 5 of the reforming zone. For example, in one embodiment of the present invention, the reforming stage is ended when the temperature at the end 5 of the reforming zone has decreased to a pre-selected temperature between about 700° C. and about 1200° C. In embodiment (b), the reforming stage duration is adjusted based on a measured feature that reflects the overall (time-averaged) performance or the system. This may be an average product composition such as $CH_4$, $H_2$, or CO. In one embodiment of the present invention, the reforming stage duration is adjusted based on the time-averaged concentration of $CH_4$ in the product, using control strategies known in the art to shorten or lengthen the duration to achieve a predetermined target $CH_4$ amount. In a preferred embodiment, the target $CH_4$ amount is set at an amount that represents between about 1% and about 15% of the hydrocarbonaceous feed carbon. In case (c), the reforming stage duration is of fixed length, at a value that is predetermined to be acceptable for the space velocity of the operation. In one embodiment the present invention, the reforming step duration is fixed at a duration between about 0.1 sec and less than about 60 seconds and preferably between about 1.0 and 30 seconds.

After the synthesis gas is collected via an exit conduit 17 at the second end 9 of the recuperating zone 7, the second stage of the cycle, also called the regeneration stage begins. The regeneration stage, illustrated in FIG. 1b, basically involves transferring this heat from the recuperating zone 7 to the reforming zone 2 and combusting fuel to further heat the reforming zone 2. In so doing, temperature gradients 25 and 26 move across the zones 7, 2 respectively similar to but in opposite directions to gradients 23 and 24 during reforming. The fuel used in the regenerating stage can be any of the hydrocarbons used as feeds for the reforming stage, as well as non-reformable fuels, such as hydrogen and carbon monoxide. Regeneration feed temperatures generally range from about 20° C. to about 600° C., such as from about 150° C. to about 450° C.

In the regeneration stage, an oxygen-containing gas, such as air, is introduced via a conduit 19 into the second end 9 of the recuperating zone 7. This gas flows across the recuperating zone 7 and combusts with the regeneration fuel substantially at a region proximate the interface 13 of the two zones 2 and 7. The term, "region proximate", in the present invention, means the region of the zones 2, 7 in which regeneration stage combustion will achieve the following two objectives: (a) the heating of the reforming zone such that end 5 of the reforming zone 2 is at a temperature of at least 800° C., and preferably at least 1000° C. at the end of the regeneration step; and (b) the cooling of the recuperating zone to a sufficient degree that it can perform its function of accepting synthesis gas sensible heat in the subsequent reforming step. Depending on specific regeneration embodiments described herein, the region proximate to the interface can include from 0% to about 50% of the volume of the recuperating zone 7 and can include from 0% to about 50% of the volume of the reforming zone 2. In a preferred embodiment of the present invention, greater than 90% of the regeneration stage combustion occurs in a region proximate to the interface, the volume of which region includes less than about 20% the volume of the recuperating zone 7 and less than about 20% the volume of reforming zone 2.

The location of combustion may be fixed by introduction of the fuel at, or substantially at, the end 11 of the recuperating zone, while the other component, e.g., the oxygen-containing gas may be introduced at the end 9 of the recuperating zone 7. The presence of catalyst in the reforming zone can also be used to initiate combustion at that location, and a space between the reforming and recuperating zones can be added and designed to further stabilize the combustion process and confine the combustion to the area proximate to the interface 13. In yet another embodiment, the location of combustion is fixed by mechanical design of the recuperating zone. In this design, the fuel and oxygen-containing gas are both introduced at the end 9 of the recuperating zone but are directed into separate channels (not shown) to deter combustion until the feeds combine at the interface 13 of the zones. At that location, flame holders (not shown) or a catalyst in the reforming zone will ensure that the combustion occurs.

The combustion of the fuel and oxygen-containing gas creates a hot flue gas that heats the reforming zone 2 as the flue gas travels across that zone. The flue gas then exits through the first end 3 of the reforming zone 2 via a conduit 27. The composition of the oxygen-containing gas/fuel mixture is adjusted to provide the desired temperature of the reforming zone. The composition and hence temperature is adjusted by means of the proportion of combustible to non-combustible portions of the mixture. For example, non-combustible gases such as $H_2O$, $CO_2$, and $N_2$ can be added to the mixture to reduce combustion temperature. In a preferred embodiment, non-combustible gases are obtained by use of steam, flue gas, or oxygen-depleted air as one component of the mixture. When the hot flue gas reaches the temperature gradient within the reformer, the gradient moves further across the bed. The outlet temperature of the flue gas will be substantially equal to the temperature of the reforming zone 2 near the inlet end 3. At the beginning of the regeneration step, this outlet temperature will be substantially equal to the inlet temperature of the reforming feed of the preceding, reforming, step. As the regeneration step proceeds, this outlet temperature will increase slowly and then rapidly as the temperature gradient reaches end 3, and can be 50–500° C. above the temperature of the reforming feed by the end of the regeneration stage.

There are alternative means for determining the end of the regeneration stage. In general, the regeneration stage is terminated when sufficient heat has been supplied or conveyed to the reforming bed to enable the carrying out of the reforming step. The point in time at which the regeneration stage is ended, and thus the duration of the regeneration stage, may be chosen (a) as a response to the time-varying performance of the reformer during each regeneration stage; or (b) based on overall (time-averaged) performance or the system; or (c) fixed as a constant regeneration stage duration.

In embodiment (a), some feature of the operation is monitored that is related to the regeneration performance. This feature could be a composition such as $O_2$, $CH_4$, $H_2$, or CO, or could be a temperature such as the temperature at the end 3 of the reforming bed. In one embodiment of the present invention, the regeneration stage is ended when the temperature at the end 3 of the reforming bed has increased to a pre-selected temperature between about 200° C. and about 800° C.

In embodiment (b), the regeneration stage duration is adjusted based on a measured feature that reflects the overall (time-averaged) performance of the system. This feature may be an average product composition such as $CH_4$, $H_2$, or CO, or some other system measurement. In one embodiment of the present invention, the regeneration stage duration is adjusted based on the time-averaged concentration of $CH_4$ in the product, using control strategies known in the art to shorten or lengthen the duration to achieve the target $CH_4$ amount. In a preferred embodiment, the target $CH_4$ amount is set at an amount that represents between about 1% and about 15% of the hydrocarbonaceous feed carbon.

In embodiment (c), the regeneration stage duration is of fixed length, at a value that is predetermined to be acceptable for the space velocity of the operation. In one embodiment the present invention, the regeneration stage duration is fixed at a duration between about 0.1 second and about 120 seconds and preferably about 1 to about 60 seconds. In all of these cases, but particularly in embodiment (c), it is preferable to also adjust the regeneration flow rates to increase or decrease the amount of heat added to the bed during the stage—in a manner similar to that described with respect to adjustment of duration in embodiment (b), above. In a further embodiment of the present invention, the regeneration step duration is fixed at a duration between about 1 second and about 60 seconds, and the regeneration flow rate is adjusted over time so that the time-average concentration of $CH_4$ in the reforming product approaches a target $CH_4$ amount that is set at an amount that represents between about 1% and about 15% of the hydrocarbonaceous feed carbon.

The reforming zone is now, once again, at reforming temperatures suitable for catalytic reforming.

In one embodiment, the air required for the regeneration stage is provided by means of blower equipment. The regeneration flue gas may then be directed to a gas expander to recover work energy that may be used to drive the air blower. Conveniently, this blower-expander pair is mechanically coupled to provide for improved cost or efficiency. In such an embodiment, the pressure of regeneration stage is typically from about 200 to about 1,000 kPa.

In another embodiment, this blower-expander function is provided by integrating the reformer regeneration system with a gas turbine. Gas turbines operate by compressing air to moderate pressure (about 700 to about 3,000 kPa), combusting a fraction of that air with fuel such that the combined stream of air and combustion product is heated to elevated temperature (about 900 to about 1300° C.), and then expanding the combined stream in a turbine resulting in mechanical power sufficient to drive the compressor and have residual power that may be used for electricity manufacture or other purposes. It is known in the art that hot compressed air can be withdrawn from gas turbines, used in outside processes, and returned with some composition and condition changes to the turbine to fulfill its role as combustion diluent and expansion fluid.

It is desirable to carry out the cyclic reforming process with a pressure swing. By pressure swing, is meant operating the two stages of the cycle at different pressures. This is advantageous because it is costly to compress air to high pressure, while it is desirable to have synthesis gas at high pressure. Thus, in a preferred embodiment, the reforming stage is carried out at higher pressures than the regeneration stage. The pressure swing is enabled because of the large volumetric heat capacity difference between the solid bed packing materials and the gas. For example, the reforming stage may be conducted at a pressure of about 1000 kPa to about 10,000 kPa, such as about 2000 kPa to about 7,500 kPa, whereas the regeneration stage is conducted at a pressure of about 100 kPa to about 2,000 kPa, such as about 200 kPa to about 1500 kPa.

The space velocity of a system is typically expressed on an hourly basis as the standard volumetric gas flow rate of feed divided by the volume of catalyst bed, called gaseous hourly space velocity, or GHSV. Space velocity can also be defined in terms of the hydrocarbon component of feed. As so defined, the GHSV for a methane feed would be the standard hourly volumetric gas flow rate of methane divided by the bed volume. As used herein, the term space velocity, abbreviated as $C_1$GHSV, refers to the space velocity of any hydrocarbon feed placed on a $C_1$ basis. As such, the hydrocarbon feed rate is calculated as a molar rate of carbon feed, and standard volume rate calculated as if carbon is a gaseous species. For example, a gasoline feed having an average carbon number of 7.0 that is flowing at a gaseous flow rate of 1,000 NL/hr into a 1.0L bed would be said to have a space velocity of 7,000. This definition is based on feed flow during the reforming step and wherein the bed volume includes all catalysts and heat transfer solids in the reforming and recuperating zones. In the steam reforming process of the invention, the space velocity, $C_1$GSHSV, typically ranges from about 500 to about 150,000, preferably from about 1,000 to about 100,000, and most preferably from about 2,000 to about 50,000.

In a preferred embodiment pressure swing reforming is conducted under bed packing and space velocity conditions that provide heat transfer rates, as characterized by a heat transfer parameter, $\Delta T_{HT}$, of between about 0.1° C. to about 500° C., and more preferably between about 0.5° C. and 40° C. The parameter $\Delta T_{HT}$ is the ratio of the bed-average volumetric heat transfer rate that is needed for reforming, H, to the volumetric heat transfer coefficient of the bed, $h_v$. The volumetric heat transfer rate that is needed for reforming is calculated as the product of the space velocity with the heat of reforming (on heat per $C_1$ volume basis). For example, H=4.9 cal/cc/s=2.2 cal/cc*8000 $hr^{-1}$/3600 s/hr, where 2.2 cal/cc is the heat of reforming of methane per standard volume of methane, and 8000 is the $C_1$GHSV of methane. When the duration of reform and regeneration stages is comparable, the value of H will be comparable in the two steps. The volumetric heat transfer coefficient of the bed, $h_v$, is known in the art, and is typically calculated as the product of an area-based coefficient (e.g. cal/$cm^2$s° C.) and a specific surface area for heat transfer ($a_v$, e.g. $cm^2/cm^3$), often referred to as the wetted area of the packing.

Bed packing materials suitable for use in the reforming and recuperating zones of the steam reformer are typically chosen so as to satisfy several characteristics. For example, a bed packing material should have the ability to cycle repeatedly between high temperatures (e.g., $\geq 1000°$ C.) and low temperatures (e.g., $\leq 600°$ C.), provide a high wetted area ($\geq 6$ $cm^{-1}$), have a high volumetric heat transfer coefficient (e.g., $\geq 0.02$ cal/$cm^3$s° C., such as $\geq 0.05$ cal/$cm^3$s° C., particularly $\geq 0.10$ cal/$cm^3$s° C.), have a low resistance to flow (low pressure-drop), have operating temperatures consistent with the highest temperatures encountered during regeneration, and a have high resistance to thermal shock. Furthermore, it is preferred that the material have high heat capacity (e.g., $\geq 0.10$ cal/$cm^3$° C., such as $\geq 0.20$ cal/$cm^3$° C.). Additionally, the bed packing material must also provide sufficient support for the reforming catalyst in the reforming bed. These requirements are met via control of the shape, size, and composition of the bed packing materials.

The shape and size of the bed packing material impacts the bed's heat transfer capability and flow resistance. This is because packing shape and size influence how the fluid flows through the packing, including, most importantly, the size and turbulence in the fluid boundary layers that are the primary resistance to heat, mass and momentum transfer between fluid and solid. Furthermore, the size of the materials also impacts the thermal shock resistance of the bed, because larger structures are sometimes susceptible to thermal shock. The shape impacts the bed heat capacity through its relationship with bed void volume. The design of advantageous packing shapes is well know in the art.

Examples of suitable packing materials include honeycomb monoliths, which have straight channels to minimize pressure drop and enable greater reactor length. Suitable honeycomb monoliths have channel densities that range from about 100 channels/in$^2$ to about 3200 channels/in$^2$ (15–500 channels/cm$^2$). In an alternative embodiment, more tortuous packing, such as foam monoliths and packed beds may be employed. Suitable foam monoliths have pore densities that range from about 4 to about 40 pores/cm. Typical packed beds for use in the present invention have a packing with a wetted surface area that ranges from about 6 to about 100 cm$^{-1}$.

The composition of the bed packing material is important to operating temperature and thermal shock resistance. Thermal shock resistance is generally greatest for materials having low coefficients of thermal expansion, because it is the temperature-induced change in size that stresses a component when temperatures are changing due to cycling. Ceramic materials have been developed that are resistant to combustion temperatures and thermal shock, particularly for application in engine exhaust filters and regenerative thermal oxidizers. Cordierite materials (magnesium aluminum silicates) are preferred for their very low coefficients of thermal expansion. Preferred materials of construction include aluminum silicate clays, such as kaolin, aluminum silicate clay mixed with alumina, or aluminum silicate clay and alumina mixed with silica and optionally zeolites. Other candidate materials of construction include mullite, alumina, silica-alumina, zirconia, and generally any inorganic oxide materials or other materials stable to at least 1000° C. The bed packing material of the recuperating zone can either be the same or different from the packing material of the reforming zone.

The configuration of the beds within the reforming and recuperating zones may take the many forms that are known in the art. Acceptable configurations include horizontal beds, vertical beds, radial beds, and co-annular beds. Packing may be monolithic or particulate in design. Particulate packing may become fluidized during some steps of the present invention. In a preferred embodiment, bed packing is maintained in a fixed arrangement.

Suitable catalysts for use in the steam reforming stage of the present process comprise noble, transition, and Group VIII components, as well as Ag, Ce, Cu, La, Mo, Mg, Sn, Ti, Y, and Zn, or combinations thereof, as well as other metal and non-metal compounds added to stabilize and/or enhance catalytic performance. As used herein, the term component relates to a metal or metal oxide thereof. Preferred catalyst systems include Ni, NiO, Rh, Pt, and combinations thereof. These materials may be deposited or coated on, or in, catalyst supports well known in the art.

It is to be appreciated that the arrangement shown in FIGS. 1(a) and (b) represents a simple pressure swing reformer. In practice, the reformer would typically have a plurality of reactors, each including reforming and recuperating zones, and would be operated so that one or more reactors would be executing the regeneration stage at the same time as one or more reactors are executing the reforming stage. This use of multiple reactors allows a continuous flow of reformed product to the methanol synthesis reactor notwithstanding the cyclical operation of each zone. Appropriate valving is used to control the flow of the various streams flowing to and from the reactors.

Methanol Synthesis

The syngas produced during the reforming stage of the cyclic steam reformer described above is sent to a methanol synthesis process and converted to methanol. The methanol synthesis process is accomplished in the presence of a methanol synthesis catalyst.

In one embodiment, the syngas is sent as is to the methanol synthesis process. In another embodiment, the hydrogen, carbon monoxide, and/or carbon dioxide content of the syngas is adjusted for efficiency of conversion. Desirably, the syngas input to the methanol synthesis reactor has a molar ratio of hydrogen ($H_2$) to carbon oxides (CO+ $CO_2$) in the range of from about 0.5:1 to about 20:1, preferably in the range of from about 2:1 to about 10:1. In another embodiment, the syngas has a molar ratio of hydrogen ($H_2$) to carbon monoxide (CO) of at least 2:1. Carbon dioxide is optionally present in an amount of not greater than 50% by weight, based on total weight of the syngas.

Desirably, the stoichiometric molar ratio is sufficiently high so as maintain a high yield of methanol, but not so high as to reduce the volume productivity of methanol. Conveniently, the syngas fed to the methanol synthesis has a stoichiometric molar ratio (i.e., a molar ratio of $H_2$:(2CO+ $3CO_2$)) of from about 1.0:1 to about 2.7:1, such as from about 1.1 to about 2.0.

In one embodiment, the catalyst used in the methanol synthesis process includes an oxide of at least one element selected from the group consisting of copper, silver, zinc, boron, magnesium, aluminum, vanadium, chromium, manganese, gallium, palladium, osmium and zirconium. Conveniently, the catalyst is a copper based catalyst, such as in the form of copper oxide.

In another embodiment, the catalyst used in the methanol synthesis process is a copper based catalyst, which includes an oxide of at least one element selected from silver, zinc, boron, magnesium, aluminum, vanadium, chromium, manganese, gallium, palladium, osmium and zirconium. Conveniently, the catalyst contains copper oxide and an oxide of at least one element selected from zinc, magnesium, aluminum, chromium, and zirconium. In one embodiment, the methanol synthesis catalyst is selected from the group consisting of: copper oxides, zinc oxides and aluminum oxides. More preferably, the catalyst contains oxides of copper and zinc.

In yet another embodiment, the methanol synthesis catalyst comprises copper oxide, zinc oxide, and at least one other oxide. Conveniently, the at least one other oxide is selected from zirconium oxide, chromium oxide, vanadium oxide, magnesium oxide, aluminum oxide, titanium oxide, hafnium oxide, molybdenum oxide, tungsten oxide, and manganese oxide.

In various embodiments, the methanol synthesis catalyst comprises from about 10 wt % to about 70 wt % copper oxide, such as from about 15 wt % to about 68 wt % copper oxide, for example from about 20 wt % to about 65 wt % copper oxide based on total weight of the catalyst.

In one embodiment, the methanol synthesis catalyst comprises from about 3 wt % to about 30 wt % zinc oxide, such as from about 4 wt % to about 27 wt % zinc oxide, for example from about 5 wt % to about 24 wt % zinc oxide based on total weight of the catalyst.

In embodiments in which copper oxide and zinc oxide are both present in the methanol synthesis catalyst, the ratio of copper oxide to zinc oxide can vary over a wide range. Typically in such embodiments, the methanol synthesis catalyst comprises copper oxide and zinc oxide in a Cu:Zn atomic ratio of from about 0.5:1 to about 20:1, such as from about 0.7:1 to about 15:1, for example from about 0.8:1 to about 5:1.

The methanol synthesis catalyst is made according to conventional processes. Examples of such processes can be found in U.S. Pat. Nos. 6,114,279; 6,054,497; 5,767,039; 5,045,520; 5,254,520; 5,610,202; 4,666,945; 4,455,394; 4,565,803; 5,385,949, with the descriptions of each being fully incorporated herein by reference.

In one embodiment, the syngas formed in the syngas conversion plant is cooled prior to being sent to the methanol synthesis reactor. Preferably, the syngas is cooled so as to condense at least a portion of the water vapor formed during the syngas process.

The methanol synthesis process implemented in the present invention can be any conventional methanol synthesis process. Examples of such processes include batch processes and continuous processes. Continuous processes are preferred. Tubular bed processes and fluidized bed processes are particularly preferred types of continuous processes.

The methanol synthesis process can be conducted over a wide range of temperatures and pressures. Suitable temperatures are in the range of from about 150° C. to about 450° C., such as from about 175° C. to about 350° C., for example from about 200° C. to about 300° C. Suitable pressures are in the range of from about 1,500 kPa to about 12,500 kPa, such as from about 2,000 kPa to about 10,000 kPa, for example 2,500 kPa to about 7,500 kPa. Gas hourly space velocities vary depending upon the type of process that is used, but generally the gas hourly space velocity of flow of gas through the catalyst bed is in the range of from about 50 $hr^{-1}$ to about 50,000 $hr^{-1}$, such as from about 250 $hr^{-1}$ to about 25,000 $hr^{-1}$, more preferably from about 500 $hr^{-1}$ to about 10,000 $hr^{-1}$.

In addition to the desired methanol product, the tail gas from the methanol synthesis process comprises unconverted carbon monoxide, carbon dioxide and hydrogen from the synthesis gas input, and unconverted hydrocarbon from the reformer.

Methanol synthesis is an exothermic process and it is necessary to limit the amount of reaction occurring in a bed of catalyst and/or to cool the bed, to avoid overheating the catalyst. To this end, a variety of reactor types may be employed. For example it is possible to employ a reactor with means to inject cool quench gas (generally a mixture of make-up gas and unreacted recycle gas) into the catalyst bed or between beds. Examples of such quench bed reactors are described in GB 1105614, EP 0297474, EP 0359952 and U.S. Pat. No. 4,859,425. It is also known to employ reactors having heat exchangers within the beds so that heat evolved by the reaction is transferred to a coolant. Thus in the arrangement described in U.S. Pat. No. 4,778,662 the synthesis reactor has coolant tubes which extend through at least the inlet part of the catalyst bed and open into the space above the inlet to the catalyst bed: the coolant is the mixture of recycled unreacted gas and make-up gas so that the reactants are heated to the desired inlet temperature by the evolved heat. In the arrangement described in GB 2046618 the catalyst is disposed as a single bed through which the reactants flow radially and heat exchange tubes are provided through which a coolant, e.g. pressurised boiling water, is circulated.

Integration of Reforming and Methanol Synthesis Processes

In accordance with the invention, the cyclic reforming and methanol synthesis processes described above are integrated by separating part of the hydrogen contained in the synthesis gas stream produced during each reforming stage of the steam reformer and/or part or all of the hydrogen contained in the tail gas stream from the methanol synthesis process and using at least part of this hydrogen as fuel for the regeneration stage of said pressure swing reformer. Embodiments of such integration are shown in FIGS. 2 and 3.

Figure 2:
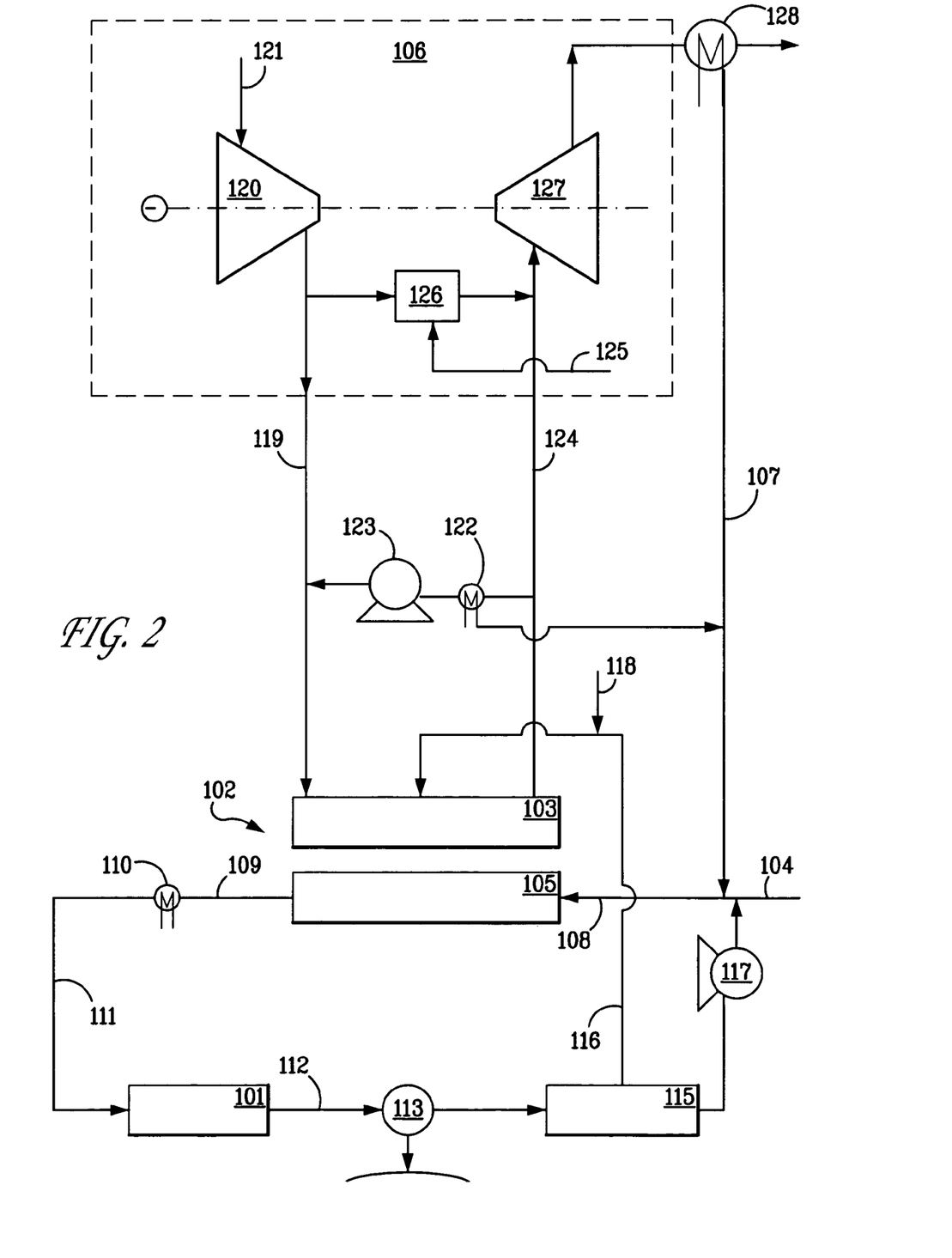
FIG. 2 is a schematic illustration of a process according to a first embodiment of the invention for integrating a pressure swing reforming process with methanol synthesis process.
Figure 3:
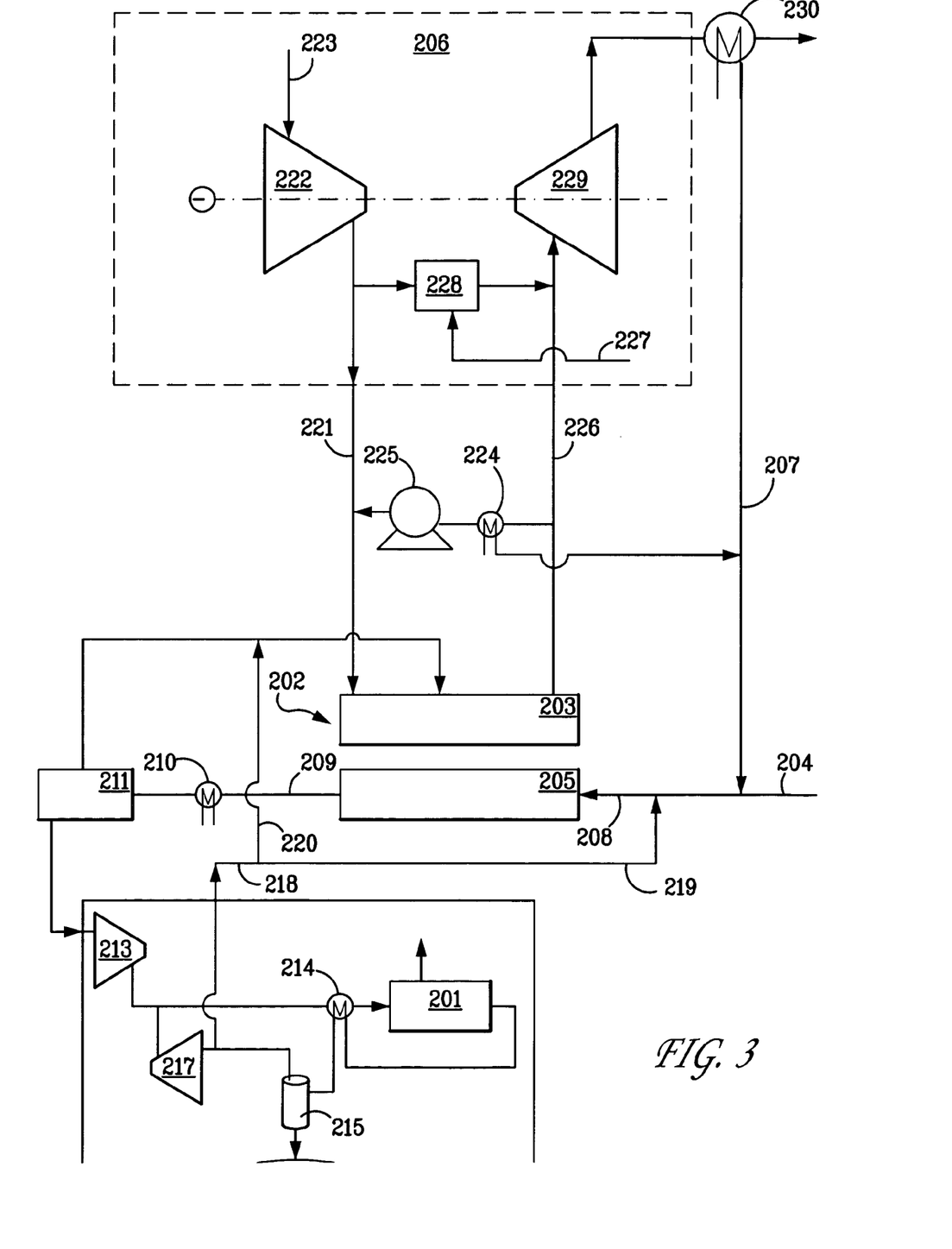
FIG. 3 is a schematic illustration of a process according to a second embodiment of the invention for integrating a pressure swing reforming process with methanol synthesis process.

Referring to FIG. 2, an integrated process is shown in which hydrogen is separated from the tail gas of a methanol synthesis reactor 101 and is recycled to fuel the regenerating stage 103 of a pressure swing reformer 102. In the process shown in FIG. 2, the reforming stage of the reformer 102 is fed via line 108 with a mixture comprising steam 107, fresh hydrocarbon feed 104, typically methane, and recycle hydrocarbon and syngas remaining after separation of hydrogen from the methanol tail gas. The steam 107 may be raised from the heat in the exhaust of a gas turbine 106 via a heat exchanger 128, from the heat in the recycle flue gas from the regenerating stage 103 via a heat exchanger 122 and/or from the heat evolved in the methanol synthesis reactor 101, as is well known in the methanol manufacturing art. The synthesis gas exiting the reformer 103 may be cooled by heat exchange to preheat the reforming stage feed (heat exchanger not shown) and is then passed via line 109 to a heat exchanger 110 to further cool the synthesis gas and remove water therefrom.

After passage through the heat exchanger 110, the synthesis gas is fed by line 111 to the methanol synthesis reactor 101 where the synthesis gas is converted to methanol. The tail gas exiting reactor 101 is cooled and fed via line 112 to a gas/liquid separator 113 where the methanol is removed as a liquid fraction and passed to a product tank 114, while the remaining gaseous fraction, containing unreacted hydrocarbon feed, CO, $CO_2$ and $H_2$, is fed to a hydrogen separator 115. Hydrogen is removed from the tail gas in the separator 115 and is fed via line 116 to the regenerating stage 103 of the pressure swing reformer 102. The remainder of the tail gas is compressed in a compressor 117 and then recycled to line 108 to supplement the fresh hydrocarbon feed to the reforming stage 105.

Supplemental fuel, normally the same hydrocarbon used as the feed to the reforming stage 105, is fed as required to the regenerating stage 103 by way of line 118. In addition, the hot air required to combust the fuel is fed to the regenerating stage 103 via line 119 from the gas turbine 106 which serves to heat and compress ambient air supplied to the turbine compressor 120 via line 121. The flue gas generated by the combustion of the fuel in the regenerating stage 103 is partly recycled to line 119 by way of a heat exchanger 122 and a recycle blower 123 and is partly fed via line 124 to the turbine 127 to power the turbine and drive the compressor 120. Additional fuel may if desired be fed by line 125 to burner 126 to provide additional power to drive the turbine 127. The heat exchanger 122 is conveniently used to provide additional steam to the reforming zone 105. In addition, the recycle blower may be driven by the turbine 106.

It is to be understood FIG. 2 provides a simplified illustration of the pressure swing reforming process by using two blocks 103 and 105 to represent the regenerating stage and reforming stage respectively. In fact, block 103 represents all the reactors (all the zones) that are executing the regeneration stage at a given moment in time, while the block 105 represents all the reactors (all the zones) that are executing the reforming stage at the same moment in time. Thus, a feed to the regenerating stage is shown as entering block 103 and a feed to the reforming stage is shown as entering block 105. Which physical reactors and zones are actually entered is controlled by valves and depends on which physical reactors are executing those stages at that moment in time.

FIG. 3 shows an alternative process for integrating a methanol synthesis reactor 201 with a pressure swing reformer 202 in which part of the hydrogen in the synthesis gas generated in the reforming stage 205 of the reformer is recycled as fuel to the regenerating stage 203 of the reformer before the synthesis gas is fed to the methanol synthesis reactor 201. Thus, referring to FIG. 3, the reforming stage 205 is fed via line 208 with a mixture comprising steam 207, fresh hydrocarbon feed, typically methane, and tail gas from the methanol synthesis reactor 201 recycled via line 219. The steam 207 may be raised from the heat in the exhaust of a gas turbine 206 via a heat exchanger 230, from the heat in the recycle flue gas from the regenerating stage 203 via a heat exchanger 224 and/or from the heat evolved in the methanol synthesis reactor 201, as is well known in the methanol manufacturing art. The synthesis gas exiting the reforming stage 205 may be cooled by heat exchange to preheat the reforming stage feed (heat exchanger not shown) and is then passed via line 209 to a heat exchanger 210 to further cool the synthesis gas and remove water therefrom.

The reforming process of the embodiment of FIG. 3 is therefore essentially the same as that of FIG. 2 embodiment. However, in the FIG. 3 embodiment, after passage through the heat exchanger 210, the synthesis gas is fed to a hydrogen separator 211 where part of the hydrogen is removed from the synthesis gas and fed via line 212 to the regenerating stage 203 of the pressure swing reformer 202. The hydrogen-reduced synthesis gas exiting the separator 211 is then compressed by a compressor 213, that is conveniently driven by the turbine 206, and heated in a heat exchanger 214 before passing to the methanol synthesis reactor 201. The tail gas from the reactor 201 is initially cooled in the heat exchanger 214 and then fed to a gas/liquid separator 215 where the methanol is removed as a liquid fraction and passed to a product tank 216. After removal of the methanol product, the remaining tail gas is recycled by way of a further compressor 217, again conveniently driven by the turbine 206, to the methanol synthesis reactor 201. A purge stream 218 is, however, conveniently removed from this recycle stream, with part of the stream 218 being fed via line 219 to the reformer to supplement the fresh hydrocarbon feed to the reforming stage 205, and the remainder of the stream 218 being fed by line 220 to the regenerating stage 205 to supplement the hydrogen from line 212.

The hot air required to combust the fuel in the regenerating stage 203 is provided via line 221 from the gas turbine 206 which serves to heat and compress ambient air supplied to the turbine compressor 222 via line 223. The flue gas generated by the combustion of the fuel in the regenerating stage 203 is partly recycled to line 221 by way of a heat exchanger 224 and compressor 225 and is partly fed via line 226 to the turbine 229 to power the turbine and drive the compressor 222. Additional fuel may if desired be fed by line 227 to a burner 228 to provide additional power to drive the turbine 229. The heat exchanger 224 is conveniently used to provide additional steam to the reforming stage 205.

In reference to FIGS. 2 and 3, it is understood that further steps, well known in the art of methanol manufacture, may be applied to the process. These steps may include, for example, methanol purification steps or additional heat exchange steps to more efficiently utilize the heat content of the streams in the process.

Integrated Process for Producing Methanol and Converting Methanol to Olefins

In one embodiment, the present invention is directed to an integrated process for producing methanol by a combination of cyclic steam reforming and methanol synthesis and for converting the resultant methanol to olefins (MTO).

Typically, molecular sieve catalysts have been used to convert methanol and other oxygenate compounds to light olefins. Silicoaluminophosphate (SAPO) molecular sieve catalysts are particularly desirable in such conversion processes, because they are highly selective in the formation of ethylene and propylene. A non-limiting list of suitable SAPO molecular sieve catalyst compositions includes SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof. Preferred molecular sieve catalyst compositions include SAPO-17, SAPO-18, SAPO-34, SAPO-35, SAPO-44, the substituted forms thereof, and mixtures thereof.

Although the present embodiment is specifically directed to combining a methanol synthesis system with an MTO reaction system, one or more additional components may be included in the methanol-containing feedstock that is directed to the MTO reaction system. For example, the feedstock can contain, in addition to methanol, one or more aliphatic-containing compounds such as alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, such as from 1 to 20 carbon atoms, for example from 1 to 10 carbon atoms, and particularly from 1 to 4 carbon atoms. Non-limiting examples of suitable additional aliphatic-containing compounds include alcohols such as ethanol, n-propanol and isopropanol; alkyl-mercaptans such as methyl mercaptan and ethyl mercaptan; alkyl-sulfides such as methyl sulfide; alkyl amines such as methyl amine; alkyl ethers such as DME, diethyl ether, di-isopropyl ether and methylethyl ether; alkyl-halides such as methyl chloride and ethyl chloride; alkyl ketones such as dimethyl ketone; alkyl-aldehydes such as formaldehyde and acetaldehyde, and various acids such as acetic acid.

In the MTO process, the various feedstocks discussed above are converted primarily into one or more olefins. The olefins produced from the feedstock typically have from 2 to 30 carbon atoms, such as from 2 to 8 carbon atoms, for example 2 to 6 carbon atoms, preferably 2 to 4 carbons atoms, and more preferably are ethylene and/or propylene.

The methanol-containing feedstock may also contain one or more diluents, typically used to reduce the concentration of the methanol in the feedstock. The diluents are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. The diluent may be used either in a liquid or a vapor form, or a combination thereof. The diluent is either added directly to a feedstock entering into a reactor or added directly into a reactor, or added with a molecular sieve catalyst composition. Typically, the amount of diluent in the feedstock is in the range of from about 1 to about 99, such as from about 1 to 80 mole percent, for example from about 5 to about 50, conveniently from about 5 to about 25 mole percent based on the total number of moles of the feedstock and diluent.

In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a methanol-containing feedstock to olefins in the presence of a molecular sieve catalyst composition may be carried out as a fixed bed process or a fluidized bed process (including a turbulent bed process), such as a continuous fluidized bed process. The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in, for example, U.S. Pat. No. 4,076,796, U.S. Pat. No. 6,287,522 (dual riser), and Fluidization Engineering, D. Kunii and O. Levenspiel, Robert E. Krieger Publishing Company, New York, N.Y. 1977, which are all herein fully incorporated by reference. The preferred reactor type are riser reactors generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

The conversion temperature employed in the MTO process may vary widely but typically is in the range of from about 392° F. (200° C.) to about 1832° F. (1000° C.), such as from about 482° F. (250° C.) to about 1472° F. (800° C.), for example from about 572° F. (300° C.) to about 1202° F. (650° C.), conveniently from about 662° F. (350° C.) to about 1112° F. (600° C.), particularly from about 662° F. (350° C.) to about 1022° F. (550° C.). Similarly, the conversion pressure can vary over a wide range including autogenous pressure. Typically the conversion pressure employed is in the range of from about 0.1 kPaa to about 5 MPaa, such as from about 5 kPaa to about 1 MPaa, for example from about 20 kPaa to about 500 kPaa, based on the partial pressure of the feedstock exclusive of any diluent therein.

The weight hourly space velocity (WHSV) is defined as the total weight of the feedstock excluding any diluents to the reaction zone per hour per weight of molecular sieve in the molecular sieve catalyst composition in the reaction zone. The WHSV is generally maintained at a level sufficient to keep the catalyst composition in a fluidized state within a reactor. Typically, the WHSV ranges from about 1 hr$^{-1}$ to about 5000 hr$^{-1}$, such as from about 2 hr$^{-1}$ to about 3000 hr$^{-1}$, for example from about 5 hr$^{-1}$ to about 1500 hr$^{-1}$, and conveniently from about 10 hr$^{-1}$ to about 1000 hr$^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly using the riser reactor(s), is typically at least 0.1 meter per second (m/sec), such as greater than 0.5 m/sec, for example greater than 1 m/sec, and conveniently preferably greater than 2 m/sec.

The invention will now be more particularly described with reference to the following Examples.

EXAMPLE 1

This Example provides a computer simulation of the integrated process shown in FIG. 2 using a General Electric Frame 9E Gas Turbine as the turbine 106 and assuming additional fuel is consumed in the burner 126 to provide a heat value flow to the turbine of 629 MBTU/hr. Heat values, as used herein, represent stream heat of combustion, on a lower heating value basis.

The pressure swing reformer 102 is operated as a pair of reactors, each alternating between 15 seconds in the regenerating stage 103 and 15 seconds in the reforming stage 105. Reforming and recuperation zones include a packing comprising a 1200 cell/in$^2$ (186 cell/cm$^2$) honeycomb monolith having a wall thickness of 7 mil (0.18mm), a wetted area of 41 cm$^{-1}$ and a bulk volumetric heat capacity of 0.23 cal/cc° C. The reforming zone comprises two thirds of the total bed, and comprises a rhodium catalyst supported on the honeycomb monolith. The space velocity during reforming stage, on a C1 hydrocarbon basis, is 4000 hr$^{-1}$.

Methane is fed through line 104 to the reforming stage 105 at a rate of 10,606 kgmole/hr and steam is fed through line 107 to the reforming stage 105 at a rate of 35,078 kgmole/hr. The methane is reformed in the reforming stage 105 to produce synthesis gas at a pressure of 6900 kPa and a temperature of 414° C. The methanol synthesis reactor, operated at a pressure of 6800 kPa, produces 10,131 kgmole/hr of methanol and hydrogen is recycled via line 118 at a rate of 11,978 kgmole/hr to provide fuel to the regenerating stage 103 equivalent to 2,739 MBTU/hr.

The flue gas from the regenerating stage 103 used to power the turbine 106 is at a temperature of 602° C. and a pressure of 1230 kPa and the turbine is operated to heat and compress ambient air such that the air in line 119 is at a temperature of 385° C. and a pressure of 1280 kPa. The air extracted from the turbine 106 represents 70% of the total air compressed. The combined air/recycle stream entering the regenerating stage 103 is at a temperature of 385° C. and a pressure of 1260 kPa.

Material balances in kgmoles/hr for the regenerating stage alone of the pressure swing reforming process, the complete pressure swing reforming process and for the methanol synthesis process of Example 1 are shown in Tables 1 to 3 respectively.

TABLE 1

| | Regeneration Air/Recycle Material Balance | | | |
|---|---|---|---|---|
| Stream | 121 Fresh Air | 118 Fuel | Recycle | 124 Gas Turbine Return |
| $H_2O$ | | 0 | 34,789 | 21,785 |
| $O_2$ | 7,673 | 0 | 0 | 51 |
| $N_2$ | 28,863 | 0 | 78,333 | 28,032 |
| $CO_2$ | | 460 | 3,302 | 1,253 |
| $CH_4$ | | 823 | 0 | 0 |
| CO | | 0 | 0 | 0 |
| $H_2$ | | 12,052 | 0 | 32 |
| Total | 36,536 | 13,335 | 116,435 | 51,134 |

TABLE 2

Pressure Swing Reformer Material Balance

| Stream | 108 Reformer-In | 109 Reformer-Out | Regen-In | Regen-Out |
|---|---|---|---|---|
| $H_2O$ | 35,078 | 16,131 | 34,799 | 56,564 |
| $O_2$ | | | 7,673 | 51 |
| $N_2$ | | 831 | 107,197 | 106,365 |
| $CO_2$ | 1,715 | 2,202 | 3,762 | 4,556 |
| $CH_4$ | 11,786 | 1,180 | 823 | |
| CO | 3,566 | 13,689 | | |
| $H_2$ | 8,166 | 40,327 | 12,052 | 32 |
| Total | 60,310 | 74,359 | 166,306 | 167,569 |

TABLE 3

Methanol Synthesis & Recycle Material Balance

| Stream | 111 Dry Syn Gas | 112 Product | 116 Hydrogen Recycle | Recycle to 105 |
|---|---|---|---|---|
| $H_2O$ | 111 | 137 | | 137 |
| $O_2$ | | | | |
| $N_2$ | | | | |
| $CO_2$ | 2,202 | 2,173 | 457 | 1,715 |
| $CH_4$ | 1,180 | 1,180 | | 1,180 |
| CO | 13,689 | 3,590 | | 3,590 |
| $H_2$ | 40,327 | 20,010 | 11,978 | 8,032 |
| Total | 57,509 | 27,091 | 12,436 | 14,655 |
| Methanol | | 10,131 | | |

EXAMPLE 2

This Example provides a computer simulation of the integrated process shown in FIG. 3 using a General Electric Frame 9E Gas Turbine as the turbine 206 and assuming additional fuel is consumed in the burner 227 to provide a heat value flow to the turbine of 923 MBTU/hr.

The pressure swing reformer 202 is operated as a pair of reactors, each alternating between 15 seconds in the regenerating stage 203 and 15 seconds in the reforming stage 205. Reforming and recuperation zones include a packing comprising a 1200 cell/in$^2$ (186 cell/cm$^2$) honeycomb monolith having a wall thickness of 7 mil (0.18 mm), a wetted area of 41 cm$^{-1}$ and a bulk volumetric heat capacity of 0.23 cal/cc°C. The reforming zone comprises two thirds of the total bed, and comprises a rhodium catalyst supported on the honeycomb monolith. The space velocity during reforming stage, on a C1 hydrocarbon basis, is 5000 hr$^{-1}$.

Methane is fed through line 204 to the reforming stage 205 at a rate of 14,309 kgmole/hr and steam is fed through line 207 to the reforming stage 205 at a rate of 35,683 kgmole/hr. The methane is reformed in the reforming stage 205 to produce synthesis gas at pressure of 3,650 kPa and a temperature of 359° C. Hydrogen is removed from the synthesis gas product at a rate of 13,891 kgmole/hr to provide a heat value flow to the regenerating stage 203 of 3,176 MBTU/hr. After removal of the hydrogen, the synthesis gas has a $H_2/(2CO+3CO_2)$ ratio of 1.015 and is fed to the methanol synthesis reactor system to produce 13,910 kgmole/hr of methanol in a reactor operated at a pressure of 7930 kPa. The purge stream 218 is divided such that 55% flows through line 220 to provide a heat value flow of 297 MBTU/hr to the regenerating stage 203 and 45% flows through line 219 to provide a heat value flow of 244 MBTU/hr to the reforming stage 205.

The flue gas from the regenerating stage 203 used to power the turbine 206 is at a temperature of 442° C. and a pressure of 1230 kPa and the turbine is operated to heat and compress ambient air such that the air in line 221 is at a temperature of 385° C. and a pressure of 1280 kPa. The air extracted from the turbine 106 represents 70% of total air compressed. The combined air/recycle stream entering the regenerating stage 203 is at a temperature of 325° C. and a pressure of 1260 kPa.

Material balances in kgmoles/hr for the regenerating stage alone of the pressure swing reforming process, the complete pressure swing reforming process and for the methanol synthesis process of Example 2 are shown in Tables 4 to 6 respectively.

TABLE 4

Regeneration Air/Recycle Material Balance

| Stream | 221 Fresh Air | 212 Fuel | Recycle | 226 Gas Turbine Return |
|---|---|---|---|---|
| $H_2O$ | | 2 | 34,985 | 19,345 |
| $O_2$ | 7,673 | | 0 | 57 |
| $N_2$ | 28,863 | | 72,706 | 27,994 |
| $CO_2$ | | 103 | 870 | 365 |
| $CH_4$ | | 238 | | |
| CO | | 28 | | |
| $H_2$ | | 14,364 | 1 | 31 |
| Total | 36,536 | 14,736 | 108,562 | 47,792 |

TABLE 5

Pressure Swing Reformer Material Balance

| Stream | 208 Reformer-In | 209 Reformer-Out | Regen-In | Regen-Out |
|---|---|---|---|---|
| $H_2O$ | 35,683 | 15,441 | 34,988 | 54,331 |
| $O_2$ | | | 7,673 | 57 |
| $N_2$ | | 869 | 101,569 | 100,699 |
| $CO_2$ | 85 | 1,749 | 973 | 1,235 |
| $CH_4$ | 14,506 | 434 | 238 | |
| CO | 22 | 12,400 | 27 | |
| $H_2$ | 380 | 44,388 | 14,365 | 31 |
| Total | 50,675 | 75,281 | 159,833 | 156,354 |

TABLE 6

Methanol Synthesis & Recycle Material Balance

| Stream | Dry Syn Gas | 212 $H_2$ Recycle | 218 Purge | 219 Reforming Recycle |
|---|---|---|---|---|
| $H_2O$ | 118 | | 4 | 2 |
| $O_2$ | | | | |
| $N_2$ | | | | |
| $CO_2$ | 1,749 | | 188 | 85 |
| $CH_4$ | 434 | | 434 | 196 |
| CO | 12,400 | | 51 | 23 |
| $H_2$ | 44,388 | 13,891 | 862 | 389 |
| Total | 59,089 | 13,891 | 1,539 | 695 |
| Methanol | 13,910 | | | |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for producing methanol comprising:
   (a) steam reforming a hydrocarbon in a reforming zone, and during the reforming stage, of a cyclic steam reformer having a reforming stage and a regeneration stage, said steam reforming being conducted under conditions effective to produce a first effluent stream containing synthesis gas;
   (b) combusting a fuel and an oxygen-containing gas in the regeneration stage of the reformer so as to reheat said reforming zone to a temperature sufficient for the reforming stage and generate a flue gas;
   (c) contacting at least part of said first effluent stream with a methanol synthesis catalyst under conditions effective to convert synthesis gas to methanol and form a methanol-containing stream and a tail gas stream comprising unreacted carbon monoxide and hydrogen; and
   (d) separating hydrogen from at least one of said first effluent stream and said tail gas stream and recycling at least part of said hydrogen as part of said fuel for the regeneration stage of said cyclic steam reformer.

2. The process of claim 1 wherein the reforming stage is conducted at a higher pressure than the regeneration stage.

3. The process of claim 2 wherein the reforming stage is conducted at a pressure of about 1000 kPa to about 10,000 kPa.

4. The process of claim 3 wherein the regeneration stage is conducted at a pressure of about 100 kPa to about 2,000 kPa.

5. The process of claim 2 wherein the reforming stage is conducted at a pressure of about 2000 kpa to about 7,500 kPa.

6. The process of claim 5 wherein the regeneration stage is conducted at a pressure of about 200 kPa to about 1,500 kPa.

7. The process of claim 1 wherein at least part of the oxygen employed in said regeneration stage is provided as compressed air extracted from a gas turbine.

8. The process of claim 7 wherein at least part of the flue gas produced in (b) is returned to the gas turbine.

9. The process of claim 1 wherein part of the oxygen-containing gas employed in (b) is recycled flue gas.

10. The process of claim 1 wherein part of the tail gas stream produced in (c) is returned to the reforming stage (a).

11. The process of claim 1 wherein part of the tail gas stream produced in (c) is returned to the regenerating stage (b).

12. The process of claim 1 wherein the hydrocarbon steam reformed in (a) comprises methane.

13. The process of claim 1 wherein the steam reforming (a) is conducted in the presence of a catalyst comprising Ni, NiO, Rh, Pt or a combination thereof.

14. The process of claim 1 wherein the reforming stage is conducted at a space velocity of from about 500 to about 150,000 $hr^{-1}$ based on C1 hydrocarbon feed basis.

15. The process of claim 1 wherein the reforming stage is conducted at a space velocity of from about 2,000 to about 50,000 $hr^{-1}$ based on C1 hydrocarbon feed basis.

16. The process of claim 1 wherein the methanol synthesis catalyst includes an oxide of at least one element selected from the group consisting of copper, silver, zinc, boron, magnesium, aluminum, vanadium, chromium, manganese, gallium, palladium, osmium and zirconium.

17. A process for producing methanol comprising:
   (a) providing a reforming reactor having a first zone comprising a reforming catalyst and a second zone comprising a packing material, said first and second zones being in fluid communication and said reformer being cyclable between a reforming stage and a regeneration stage;
   (b) introducing a hydrocarbon and steam into the first zone of the reforming reactor during each reforming stage and steam reforming the hydrocarbon in said first zone under conditions effective to produce a first effluent stream containing synthesis gas;
   (c) passing at least a portion of said first effluent stream from said first zone to said second zone and transferring heat from said first effluent stream to said packing material;
   (d) withdrawing the first effluent stream from the second zone;
   (e) introducing an oxygen-containing gas and fuel into the second zone of the reforming reactor during each regeneration stage under conditions to combust the fuel and reheat said first zone to a temperature sufficient for the reforming stage and produce a flue gas;
   (f) contacting at least part of said first effluent stream with a methanol synthesis catalyst in a methanol synthesis reactor under conditions effective to convert synthesis gas to methanol and form a methanol-containing stream and a tail gas stream comprising unreacted carbon monoxide and hydrogen; and
   (g) separating hydrogen from at least one of said first effluent stream and said tail gas stream; and
   (h) recycling at least part of the hydrogen separated in (g) as part of said fuel for the regeneration stage of said reforming reactor.

18. The process of claim 17 wherein the reforming stage is conducted at a higher pressure than the regeneration stage.

19. The process of claim 18 wherein the reforming stage is conducted at a pressure of about 1000 kPa to about 10,000 kPa.

20. The process of claim 19 wherein the regeneration stage is conducted at a pressure of about 100 kPa to about 2,000 kPa.

21. The process of claim 18 wherein the reforming stage is conducted at a pressure of about 2000 kPa to about 7,500 kPa.

22. The process of claim 21 wherein the regeneration stage is conducted at a pressure of about 200 kPa to about 1,500 kPa.

23. The process of claim 17 wherein at least part of the oxygen employed in said regeneration stage is provided as compressed air extracted from a gas turbine.

24. The process of claim 23 wherein at least part of the flue gas produced in (d) is returned to the gas turbine.

25. The process of claim 17 wherein part of the oxygen-containing gas employed in (b) is recycled flue gas.

26. The process of claim 17 wherein part of the tail gas stream produced in (f) is returned to the reforming stage (b).

27. The process of claim 17 wherein part of the tail gas steam produced in (f) is returned to the regenerating stage (d).

28. The process of claim 17 wherein the hydrocarbon steam reformed in (b) comprises methane.

29. The process of claim 17 wherein the reforming catalyst comprises Ni, NiO, Rh, Pt or a combination thereof.

30. The process of claim 17 wherein the reforming stage is conducted at a space velocity of from about 500 to about 150,000 hr$^{-1}$ based on C1 hydrocarbon feed basis.

31. The process of claim 17 wherein the packing material has a wetted area greater than 6 cm$^{-1}$.

32. The process of claim 17 wherein the packing material comprises a honeycomb monolith having a bulk volumetric heat capacity greater than 0.2 cal/cm$^{3\circ}$ C.

33. The process of claim 17 wherein the packing material comprises a magnesium aluminum silicate, an aluminum silicate clay, mullite, alumina, silica, silica-alumina, zirconia, a zeolite or a combination thereof.

34. The process of claim 17 wherein the reforming catalyst is supported on a further packing material.

35. The process of claim 34 wherein the further packing material has a wetted area greater than 6 cm$^{-1}$.

36. The process of claim 34 wherein the further packing material comprises a honeycomb monolith having a bulk volumetric beat capacity greater than 0.2 cal/cm$^{3\circ}$ C.

37. The process of claim 34 wherein the further packing material comprises a magnesium aluminum silicate, an aluminum silicate clay, mullite, alumina, silica, silica-alumina, zirconia, a zeolite or a combination thereof.

38. The process of claim 17 wherein the methanol synthesis catalyst includes an oxide of at least one element selected from the group consisting of copper, silver, zinc, boron, magnesium, aluminum, vanadium, chromium, manganese, gallium, palladium, osmium and zirconium.

39. A process for producing olefins comprising contacting the methanol produced by the process of claim 1 with a molecular sieve catalyst under conditions effective to convert the methanol to an olefin-containing product.

40. A process for producing olefins comprising contacting the methanol produced by the process of claim 17 with a molecular sieve catalyst under conditions effective to convert the methanol to an olefin-containing product.

* * * * *